United States Patent [19]

Mayo et al.

[11] Patent Number: 5,411,749
[45] Date of Patent: May 2, 1995

[54] HUMAN LYMPHOID TISSUE IN AN IMMUNOCOMPROMISED HOST

[75] Inventors: Susan K. Mayo, Portland, Oreg.; Reiko Namikawa; Hideto Kaneshima, both of Palo Alto, Calif.; Joseph M. McCune, San Francisco, Calif.

[73] Assignee: Systemix, Inc., Palo Alto, Calif.

[21] Appl. No.: 996,831

[22] Filed: Dec. 23, 1992

Related U.S. Application Data

[63] Continuation of Ser. No. 738,673, Jul. 31, 1991, abandoned, which is a continuation-in-part of Ser. No. 518,748, May 3, 1990, abandoned.

[51] Int. Cl.$^6$ .................... A61K 35/00; A61K 39/00; A61K 49/00
[52] U.S. Cl. ........................... 424/578; 424/9; 424/184.1; 800/2; 800/DIG. 5; 530/388.15
[58] Field of Search ............. 424/520, 578, 579, 580, 424/582, 9, 88, 184.1; 800/2, DIG. 5; 435/1

[56] References Cited

PUBLICATIONS

McCune et al., Science 241: 1632–1639 (1988).
Povlsen et al., Nature 248: 247–249 (1974).
Bosma et al., Nature 301: 527–530 (1983).
Kozbor et al., Immunology Today 4(3): 72–79 (1983).
Mosier et al., Nature 335: 256–259 (1988).
Morrison et al., Amer. N.Y. Acad. Sci. 507: 187–198 (1988).
Huse et al., Science 246: 1275–1281 (1989).

*Primary Examiner*—Jasemine C. Chambers
*Attorney, Agent, or Firm*—Bertram I. Rowland; Pamela J. Sherwood

[57] ABSTRACT

Human lymphoid tissue is introduced into an immunocompromised host to provide opportunities to investigate the effect of stimuli on the human immune system and obtain information and products from the stimulus. Particularly, methodology is provided for the production of human monoclonal antibodies by introducing lymphoid tissue into an immunocompromised host, stimulating the B-lymphocytes with an appropriate immunogen, harvesting the tissue and immortalizing and/or cloning the B-lymphocytes under conditions to obtain a stable supply of monoclonal antibodies.

4 Claims, No Drawings

HUMAN LYMPHOID TISSUE IN AN IMMUNOCOMPROMISED HOST

CROSS-REFERENCE TO RELATED APPLICATIONS

This application is a continuation of application Ser. No. 07/738,673 filed on Jul. 31, 1991, now abandoned, which application is a continuation-in-part of application Ser. No. 518,748, filed May 3, 1990, now abandoned, which is incorporated herein by reference.

INTRODUCTION

1. Technical Field

The field of this invention is the utilization of the human lymphoid system in testing human immune response and for the production of human antibodies.

2. Background

The human immune system is the guardian of human health against invasive organisms, aberrant cellular conditions, e.g. neoplasia, and the like. There is either or both a humoral and/or cellular response to a variety of pathological conditions. In the prophylactic or therapeutic treatment of these conditions, the primary focus is on the effect of the treatment on the disease state. In many cases, the treatment may have an advantageous or detrimental effect on the immune response to the condition. Studying such response is difficult until the therapy is used with human hosts.

For a number of diseases, vaccinations are provided. Frequently, there is no animal model which can provide the desired information concerning the nature of the response to the vaccine, the efficiency of the response and the overall effect of the vaccine on the host. In many instances the inability to evaluate the vaccine with animals may preclude its use as a vaccine.

In light of the uncertainties concerning therapies for humans, there is a substantial need to develop animal models which will allow for the testing of the effect of therapies on the human immune system.

The monoclonal antibody, discovered in the middle 1970's has been exploited widely in diagnostics and substantially less so in therapy. It is based on the observation that a mammalian host can be induced to make a primary immune response against any antigen by selective immunization and that the specific B cells making antibody can be immortalized by fusion to create hybridoma cell lines producing monospecific antibody against the immunogen. The original promise of a "magic bullet" has not been realized. One of the limitations on the use of monoclonal antibodies for therapy has been the immune response to heterologous antibodies. Since, for the most part, mouse antibodies are the most convenient to induce and mouse B-lymphocytes to immortalize for production of monoclonal antibodies, with few exceptions, the monoclonal antibodies which have found commercial and research use have been mouse monoclonal antibodies. The ability to prepare human monoclonal antibodies has been limited due to the inability to induce a primary immune response in vitro. There is, therefore, interest in being able to develop other techniques for producing human monoclonal antibodies, where the opportunity exists to produce antibodies of high affinity, specific for epitopes of interest, and having the human constant region and framework region of the polymorphic region.

Relevant Literature

EPO 0 322 240 describes the introduction of human fetal tissue in an immunocompromised mouse host. See also Co-pending application Ser. No. 394,939, filed Aug. 17, 1989, and co-pending application Ser. No. 462,823, filed Jan. 10, 1990, and references cited therein.

SUMMARY OF THE INVENTION

Human fetal lymphoid tissue in an immunocompromised non-primate host is provided. Immunization of human lymphoid tissue to produce a primary B-lymphocytic response to a specific epitope is described, where the lymphoid tissue is in an immunocompromised xenogeneic host. The stimulated B-lymphocytes may then be immortalized for the stable production of monoclonal antibodies. Methods for evaluating the effect of compounds and procedures on the immune system are described.

DESCRIPTION OF THE SPECIFIC EMBODIMENTS

A chimeric host comprising human fetal lymphoid solid tissue in an immunocompromised non-primate host is provided, where the lymphoid tissue is characterized by comprising at least antigen presenting cells, particularly B-lymphocytes, and T-lymphocytes, including CD4 and normally CD8 cells. The solid tissue may be used in various methodologies utilizing the immune system for the production of secreted products or for evaluating the response of the immune system, particularly the lymphoid system, although the myelomonocytic system may also be involved, to a compound or method of treatment for a diseased state which is responsive to the immune system. A single organ is used rather than a combination of interacting organs, where cells may traffic from one organ to another.

The chimeric host has a number of uses based on the presence of viable functioning human fetal lymphoid tissue in the chimeric host. The presence of antigen presenting cells and T-lymphocytes provides for the opportunity to immunize with an antigen and for the production of B-lymphocytes having the immunoglobulin locus rearranged to produce immunoglobulins having specificity for a predetermined antigen. The presence of the cells of the lymphoid lineage, particularly in conjunction with cells of the myelomonocytic lineage, allows for the evaluation of compounds and methodologies on the modulation of the immune response, up or down regulating the production of cells involved with the immune response. Thus drugs, combinations of drugs, and treatment modalities may be evaluated as to their effect on the expansion and/or inhibition of the proliferation of cells involved with the immune response.

The first aspect of the subject invention to be considered will be the production of human monoclonal antibodies. Methodology is provided for creation of human activated B-lymphocytes in vivo to any antigen and the use of the B-lymphocytes for production of human monoclonal antibodies to a predetermined epitope. Lymphoid tissue is introduced at an appropriate site of an immunocompromised mammal. Sufficient time is allowed for the lymphoid tissue to become vascularized and lymphatic vessels connected. B-lymphocytes are then activated with an appropriate immunogen having the desired epitope to stimulate B-lymphocytes producing immunoglobulin specific for the desired epitope. After a sufficient degree of stimulation, the B-lymphocytes may then be cloned or immortalized for continuous production of monoclonal antibodies. The resulting monoclonal antibodies may be screened for their binding affinity and the immortalized or cloned cells secreting the antibodies maintained by any convenient means.

Various lymphoid or other lymphocyte containing human tissue may be employed which provides for B-lymphocyte and T-lymphocyte interaction, preferably including macrophage interaction. Tissue which may be employed includes lymph node, both mesenteric and peripheral, either with or without mesentery, thymus, tonsil, spleen, pancreas, bone, etc., preferably lymph node. The tissue is preferably obtained from a fetal source, having a gestational age of at least four weeks, more usually at least about 6 weeks and ranging up to neonate tissue, depending upon the nature of the tissue or organ, preferably being fetal tissue of about 7 to 22 weeks.

For different organs, differently aged tissue may be preferred. For example, for human lymph node, the age is desirably equal to or greater than about 15 gestational weeks (g.w.), preferably 16–20 g.w.; for human thymus, from about 9 to 22 g.w., preferably less than about 20 g.w. Fetal liver tissue may find use in combination with other tissue, particularly lymph node tissue, where the lymph node tissue will generally be of an age in the range of 9–22 g.w. For bone marrow, the tissue will be about 12 to 24 g.w.

The xenogeneic host will be an immunocompromised mammal other than human. The immunocompromised host may be immunocompromised in a variety of ways, where the result will be the substantial lack of functional T- and B-lymphocytes. The xenogeneic host may have defects at various levels resulting in an immunocompromised host. The defect results in loss of functional antibody secreting lymphocytes, particularly the inability to produce antibody, as a result of a deficit in the rearrangement of the immunoglobulin or T-lymphocyte locus, in factor receptors, in T-lymphocytes, or the like.

Any mammalian host may be employed other than the presently available SCID mice and horses (equine), which host may include members of the ovine, bovine, caprine, lagomorpha, primate (other than human), porcine, canine, feline, etc. Animal hosts of particular interest are laboratory animals, such as mice, rats, guinea pigs, e.g. capybara, rabbits, as well as domestic animals, such as primates other than humans, cows, sheep, pigs, horses, or the like. Of more particular interest are those mammals which lack functional B- and T-lymphocytes as a result of a genetic defect in the ability of the lymphoid lineage to differentiate and mature from a progenitor cell. That is, the animals lack functioning lymphoid cells because of other than a lack of a thymus providing for processing of lymphoid cells. These mammals are illustrated by the CB-17 scid/scid mice. If desired, the immunocompromised host may be produced by changes induced by transformation of embryonic stem cells or introduction of transformed hematopoietic stem cells in a host lacking functional bone marrow, e.g. a lethally irradiated host. The defect may be any of a large number of genes, such as a recombinase gene, a regulatory gene for the recombinase, a gene involved in transport of the immunoglobulin, loss of exons associated with the constant regions, a lesion in the loci site for the T cell receptor and the surface immunoglobulin or the like.

Various sites may be selected for the introduction of the human tissue, where the sites are downstream from a convenient site in the blood or lymphatic system for introduction of the immunogen. Sites which have found application include the popliteal fossa, the mammary fat pad, particularly the fourth mammary fat pad, the kidney capsule, cervical and the like. Of particular interest is the popliteal fossa, where the immunogen may be introduced in the footpad and drained by the lymphatic vessel to the popliteal fossa, particularly on implanted lymph node.

The tissue may be fresh tissue, obtained within about 48 hours of death, or freshly frozen tissue, tissue frozen within about 12 hours of death and maintained at below about $-10$ degrees C., usually at about liquid nitrogen temperature ($-70$ degrees C.) indefinitely. The tissue may be from an organ implanted in a chimeric host, where the tissue may be removed from 2 to 4 weeks after implantation, or longer. In this manner, the tissue originally obtained from the host source may be greatly expanded, substantially increasing the total number of chimeric hosts which may be obtained. The tissue obtained from the chimeric host may be treated analogously to the tissue obtained from the human source. The tissue may be provided as portions of organs or complete organs, comprising or freed of attached stromal elements, generally from about 0.5 to 4 mm, more usually from about 1 to 2 mm, so that the sections can easily fit into a trocar used for implantation, usually conveniently of about 15- to 20-gauge. Normally, the tissue will not have been subject to culture in vitro for an extended period of time. In some cases, whole organ grafts may be transplanted by anastomosing donor and host blood vessels, lymphatic vessels, and the like.

Besides the lack of functional T- and B-lymphocytes, further reduction in immunocompetence may be achieved by breeding, use of natural killer deficient mutants, irradiation of the host or use of immunocytotoxic labels joined to antibodies specific for these cells to be killed, for example, lymphoid or myelomonocytic lineages. Particularly, where immunocompetence is to varying degrees provided by the tissue being introduced into the host in accordance with the subject invention, native immunocompetence can be further reduced below the low level naturally present in the host.

The host will usually be of an age less than about 25 percent of the normal lifetime of an immunocompetent host, usually about 1 to 20 percent of the normal lifetime. Generally the host will be at least about 3 weeks old and large enough to manipulate for introduction of the tissue at the desired site. For example, mice which may be considered to have about 2–4 lifetime are used at about 3 to 10, usually 4 to 8 weeks of age. Growth of the tissue within the host will vary with the organ, usually being at least about 1–2 fold.

Normally, the tissue which is introduced into the host will be allowed to grow and vascularize and have lymphatic vessels connected before immunization. Generally, at least one week will transpire, preferably at least about 2 weeks, and usually immunization will occur within 20 weeks of transplantation, more usually within 2 to 10 weeks of transplantation.

The subject methodology may be used with any compound having an epitope of interest, including epitopes common to humans. Since there is no concern about the effect of producing antibodies specific to a human protein in the subject chimeric host, one can develop antibodies to native human proteins. Immunogens of interest may be both haptens and antigens, where the haptens are modified to provide for an immune response. Compounds of interest may include small synthetic organic molecules, generally of less than about 5 kD (kilodaltons), usually less than about 2 kD, polypeptides and proteins, lipids, saccharides, and combinations thereof. The compounds may be synthetic or naturally occurring, including drugs, hormones, cytokines, surface membrane proteins, enzymes, sugar side groups, toxins, etc. The immunogen may be combined with a wide variety of adjuvants, such as complete Freund's adjuvant, specol, B. pertussis or its toxin, etc. Usually, the injection will vary widely depending upon the size of the animal, usually varying from about 10 ml to 5 ml, comprising from about 10 mg to 1 mg of the immunogen. The adjuvants will be used in conventional amounts in accordance with the nature of the adjuvant.

Administration will normally be by injection, which will usually be subcutaneous, intramuscular, intraperitoneal or intravascular, where the injection is upstream from the site of the human lymphoid tissue. One or more booster injections may be made, usually within 1 to 6, more usually 2 to 4 weeks of the previous injection, where a booster injection may have the same composition or different composition from the prior injection, by changing the concentration, adjuvant, or the like. In conjunction with administration of the immunogen, IL-6 may be administered, generally to provide a concentration in the bloodstream in the range of about 0.5–20 mg/ml.

After the immunization is complete, the tissue may be harvested and the B-lymphocytes immortalized and/or cloned as appropriate. Various fusion partners are available, which are capable of immortalizing human B-lymphocytes. See, for example, Kan-Mitchel et al., *J. Clin. Lab. Anal.* (1989), 3: 41–9. The methods employed for the fusion are to combine the B-lymphocytes with the fusion partner in the presence of a fusogen, usually a non-ionic detergent for sufficient time for fusion to occur, followed by selection of the resulting hybridomas in accordance with the nature of the marker(s) present in the fusion partner. The cells may then be subjected to limiting dilution to provide for clones free of contaminated cells, so as to result in a homogeneous antibody composition. The hybridomas may then be introduced into host animals, e.g. mice or rats, to produce ascites fluid or mechanically expanded, using spinner flasks, roller bottles, etc. The host will be immunocompromised, so as to be able to accept the neoplastic graft.

The B-lymphocytes or immortalized progeny thereof may be used as a source of DNA where the mRNA or rearranged genomic DNA may be isolated. One can determine the type of constant region for both the heavy and light chains, so as to be able to use nucleic acid probes specific for the particular type chain. A wide variety of techniques exist which allow one to probe cDNA libraries or genomic libraries for complementary sequences. Libraries can be readily prepared by fragmenting the genome or employing reverse transcriptase to produce cDNA and inserting the DNA into an appropriate cloning vector and cloning the DNA. The library may then be searched using the appropriate probes and in the case of the cDNA, identifying clones which have a full transcript. Once the DNA has been identified, it may then be used for expression by modifying the DNA as appropriate depending upon the expression host. In the case of the genomic DNA, if a mammalian cell, particularly a lymphoid cell, is to be used for expression, one may depend upon the native promoter region for expression. Alternatively, if one wishes to express the genes encoding the light and heavy chains in other than mammalian lymphoid cells or one wishes to use a different transcriptional initiation region from the native region, one can provide for a different transcriptional initiation region. In the case of the genomic DNA, one may remove the native region by primer repair, the polymerase chain reaction, restriction, or the like. One may then add the desired transcriptional initiation region, which is functional in the expression host. In the case of the cDNA, where there will be no promoter region, one may ligate the promoter region to the 5' end of the cDNA to provide for transcriptional initiation. As appropriate, one may ligate at the 3' end, a transcriptional termination region. The resulting construct may then be transformed into an appropriate expression host, which may be prokaryotic or eukaryotic. One may provide for stable extrachromosomal maintenance in the prokaryotic or eukaryotic host, by either employing a vector which allows for stable maintenance in the host or a vector which cannot be stably maintained, but includes a marker in conjunction with the gene(s) encoding the immunoglobulin chain(s), which allows for selection of those expression hosts comprising the desired gene(s). The usual markers include antibiotic resistance and complementation of auxotrophy to prototrophy.

One may express each of the chains separately or express them together in the same expression host. Where the chains are expressed separately, they may be brought together under conditions where the proper disulfide forms, so as to recreate the immunoglobulin. Where the light and heavy chains are expressed in the same expression host, one may isolate the immunoglobulin free of other proteins of the host.

One may also use the subject system to introduce greater variety to enhance desired affinities or provide for different affinities for the immunoglobulins. By using prokaryotic hosts, or eukaryotic hosts, such as yeast, one can mix the heavy and light chains from different cells expressing antibodies binding to the same epitope, so as to get unnatural combinations of light and heavy chains. These immunoglobulins may then be screened for their binding affinity, as compared to the natural combinations. Furthermore, one can modify the variable region in a variety of ways, by introducing changes, particularly in the D region of the heavy chain or the J regions of the light and/or heavy chains or even in the variable domain of the light and heavy chains. This can be done randomly by mutagenesis, where the gene for the entire chain is present in the cell, or where only the variable region is present in the cell. Alternatively, one may use site-directed mutagenesis or PCR to introduce specific changes based on the amino acid pattern observed among the immunoglobulins which bind to the particular epitope. In this way, one may splice all or portions of D domains, J domains or V domains to domains from other genes to determine whether higher affinities may be achieved. Once the genes have been mutated or modified, they may be expressed in an appropriate expression host, as described above.

For further description of this technique, see Iverson, et al., (1989) *Cold Spring Harbor Symposium on Quantitative Biology*, Vol. LVI, Cold Spring Harbor Laboratory Press, pp. 273-281; Sasty, et al., *Proc.Natl.Acad.Sci.USA* (1989) 86: 5728-5732; Huse, et al., *Science* (1989) 246: 1275-1281.

The resulting antibodies may be used in a variety of ways, both diagnostic and therapeutic. However, since other antibodies which are normally more easily obtained, such as non-human antibodies can be used in in vitro diagnostics, for the most part the subject antibodies will be used for in vivo diagnostic and therapeutic use in humans. Thus, the subject antibodies may be used in the treatment of septicemia, ablation of particular T-lymphocyte receptors, neutralizing viruses or other pathogens, for in vivo diagnoses, for targeted toxicity against neoplastic cells or precursors to such cells, passive immunization, in conjunction with transplantation, and the like. The subject antibodies may be modified by radiolabeling, conjugation to other compounds, such as biotin, avidin, enzymes, cytotoxic agents, e.g. ricin, diphtheria toxin, arbin, etc., and the like.

The subject chimeric hosts may also be used in the production of human T-lymphocytes specific for a particular target cell or a particular immunodominant sequence. These T-lymphocytes may be CD4 helper cells, CD8 suppressor cells, natural killer cells, cytotoxic T-lymphocytes, antibody dependent cytotoxic cells, tumor infiltrating lymphocytes ("TILs"), etc. The same system that is employed for the production of B-lymphocytes specific for a predetermined antigen may be employed for the production of CD4 helper cells specific for an immunodominant sequence which binds the target major histocompatibility complex to which the T-lymphocyte is restricted. Also, for the other types of T-lymphocytes, by providing for the appropriate stimulus, one may produce TILs, using neoplastic tissue in conjunction with the lymphoid tissue; for other types of T-lymphocytes, using various cytokines and/or growth factors in conjunction with a stimulus, e.g. microorganism, and the like.

The lymphoid tissue may also be used in the studies of vaccines and drugs, as to efficacy in producing an immune response and as to the effect of the drug on the immune system. For a vaccine, lymphoid tissue, such as lymph node, may be used in substantially the same manner as was described for the production of monoclonal antibodies. By providing a base line for response with a number of different vaccines one can compare vaccines as to their response in producing a primary and secondary immune response. In addition, one can immortalize the activated B-lymphocytes and screen the antibodies for their protective effect against the pathogen.

In addition, one can use the lymphoid tissue to determine the effect of drugs on the immune system. One can detect the effect of drugs on the viability of human hematopoietic cells in various tissues, the effect of the drugs upon stimulation by immunogens and/or cytokines and the like. By introducing bone comprising bone marrow in the immunocompromised host, determining the relative population of the cells in the bone marrow and the change in the population in the presence and absence of a therapeutic dosage of the drug, one can obtain an indication of the effect of the drug on the hematopoietic cells in the bone marrow. By stimulating the bone marrow with an immunogen in the presence and absence of the drug and evaluating the immune response, one can measure the effect of the drug on the humoral immune response. To measure the effect, one could determine the number of cells which have been activated to produce sIg, by preparing tissue slices, labeling the sIg for the immunogen and counting the number of cells which are specifically labeled.

The following examples are offered by way of illustration and not by way of limitation.

EXPERIMENTAL

CB-17 scid/scid mice were transplanted with mesenteric lymph nodes into the popliteal fossa region. An incision is made in the site directly over the fat pad on the back hind leg of the mouse. The main vein that runs vertically up to the trunk that rests on top of the fat pad is cauterized. An incision is made through the fat to expose the popliteal fossa lymph node (LN). The LN is removed and the human tissue is inserted at the same site. Sutures are made to close the dermal incision.

A dose of 50 mg of trinitrophenyl-keyhole limpet hemocyanin (TNP-KLH) combined with specol adjuvant (5 ml TNP-KLH [10 mg/ml] is vortexed with 6 ml specol adjuvant) was injected subcutaneously into the footpad, where the lymphatic vessels drain into the popliteal fossa lymph node. The graft in one mouse showed appropriate cellularity and was observed to contain a large number of human IgG and IgM positive cells. After 4 days from the immunization, the tissue was harvested, histologic sections prepared and these sections analyzed. The staining procedure is as follows. The immunized human graft is surgically removed from the host and snap frozen in liquid nitrogen. Tissue is sectioned 8 mm thick using a cryostat and placed on glass slides. Tissue is stored if not used promptly at $-20$ degrees C. The slides are humidified, dried and fixed in acetone for 20 min. Slides are then wet 1x PBS and incubated with trinitrophenyl-conjugated alkaline phosphatase (TNP-AP) diluted in 0.1% BSA/PBS and containing 1% normal human serum. The slides are washed 3x in 1x PBS. The development is performed using the substrate solution: naphthol-As-phosphate, fast Blue BB salt dissolved in DMF diluted in 0.05 propandiol buffer, pH 9.75, and 10 mM levamisole-Hcl. The reaction is allowed to proceed for 5-10 min and stopped by submerging the slide in 1x PBS. The slides are then counterstained with hematoxylin for 30 sec, dried and mounted with a coverslip using glycerol/gelatin.

When stained for anti-TNP producing cells, there were several very distinct positive cells. Positive cells show a blue cytoplasmic staining. The staining was shown not to be due to indigenous alkaline phosphatase by the development of the tissue with substrate alone. Blocking of the staining was also shown using 10 mg/ml of TNP-KLH, while 1 ng/ml did not inhibit the cellular staining. The double staining showed human IgM positive cells specific for TNP.

Human Fetal Bone Implantation

Human fetal long bones (17-22 g.w.) of about 1 cm in length (1-2 bones) were transplanted subcutaneously into CB 17 scid/scid mice. At different time points after transplantation, bones were taken out and cells recovered from them were stained with either human specific antibody, MEM-43, or mouse specific antibody, Ly.5.1 and analyzed by FACS or cytospin preparations. Sections from the transplants were prepared for routine histology.

Human hematopoiesis was not observed by histology or by cytospin preparations at 2-3 weeks after transplantation. The majority of cells recovered from human bone grafts were positive for MEM-43. Scatter analysis by flow cytometry did not show lymphoid or myeloid populations, suggesting that the majority of cells were non-hematopoietic in origin.

At 4-5 weeks after transplantation, signs of hematopoiesis (i.e., presence of blast cells, immature forms of myelomonocytic cells and erythroblasts) were observed in cytospin preparations in most cases analyzed. The MEM-43 positive cells in these samples showed a scatter profile similar to that of the fetal bone marrow samples. Cells of the myelomonocytic lineage, B cell lineage and the erythroid lineage were shown by immunofluorescent staining with LeuM1 (CD15), CD10 and CD19, and anti-human glycophorin A, respectively.

The above data demonstrated that human hematopoiesis is maintained inside the transplanted bones for periods of time of at least 8 weeks after implantation in the absence of other human tissue, that cells can be detected of the various lineages, and in view of the availability of human cells in the bone tissue, the effect of various compounds or conditions may be investigated in relation to the maintenance and proliferation of the hematopoietic cells.

It is obvious from the above results that the subject methodology provides for a unique way to achieve human monoclonal antibodies against any epitope of interest. Animals may be selected which are easy to handle, can be readily immunized, and the tissue harvested in accordance with conventional techniques. By employing booster shots and using a plurality of animals, a large variety of antibodies may be obtained of high affinity specific for a particular epitope or epitopes of a particular antigen. The resulting stimulated B-lymphocytes may then be used for immortalization and/or cloning to provide for a stable supply of human monoclonal antibodies.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing human antibodies, said method comprising:
    immunizing an immunocompromised chimeric mouse host comprising human fetal lymph node tissue with an immunogen; and
    harvesting said human lymph node tissue as a source of B-lymphocytes producing antibodies to said immunogen;
    wherein said chimeric mouse host is a CB.17 scid/scid, comprising vascularized and lymphatic vessel connected human fetal lymph node tissue comprising human B- and T-lymphocytes as a result of implantation of said human fetal lymph node tissue at the popliteal fossa, a vascularizable and lymphatic vessel connectable site, and capable of at least a primary immune response to an immunogen.

2. A method for producing human monoclonal antibodies, said method comprising:
    immunizing an immunocompromised CB-17 scid/scid chimetic mouse comprising human fetal lymph node tissue with an immunogen at a site upstream from vascularized and lymphatic vessel-connected human fetal lymph node tissue comprising B- and T-lymphocytes;
    harvesting said human fetal lymph node tissue as a source of B-lymphocytes producing antibodies to said immunogen; and
    cloning immunoglobulin producing B-lymphocytes for production of human monoclonal antibodies specific for an epitope of said immunogen;
    wherein said chimetic mouse is characterized by comprising vascularized and lymphatic vessel-connected human fetal lymph node tissue comprising B- and T-lymphocytes as a result of implantation of said human fetal lymph node tissue at the popliteal fossa, a vascularizable and lymphatic vessel-connectable site, and capable of at least a primary immune response to an immunogen.

3. A method according to claim 2, wherein said immunizing is injection in the footpad drained by said lymph node tissue.

4. A method according to claim 2, wherein said fetal lymph node tissue is whole lymph node.

* * * * *